(12) United States Patent
Solomon

(10) Patent No.: US 7,921,384 B2
(45) Date of Patent: Apr. 5, 2011

(54) SYSTEM, METHODS AND APPARATUSES FOR INTEGRATED CIRCUITS FOR NANOROBOTICS

(76) Inventor: Neal Solomon, Oakland, CA (US)

(*) Notice: Subject to any disclaimer, the term of this patent is extended or adjusted under 35 U.S.C. 154(b) by 382 days.

(21) Appl. No.: 11/985,036

(22) Filed: Nov. 13, 2007

(65) Prior Publication Data

US 2008/0244500 A1    Oct. 2, 2008

Related U.S. Application Data

(60) Provisional application No. 60/865,605, filed on Nov. 13, 2006, provisional application No. 60/912,133, filed on Apr. 16, 2007.

(51) Int. Cl.
*G06F 17/50* (2006.01)
(52) U.S. Cl. ............... 716/30; 716/116; 716/117
(58) Field of Classification Search ............ 716/1, 8–14, 716/16, 17, 33, 116, 117, 126; 700/245; 703/11; 901/1; 257/414, 499; 438/689
See application file for complete search history.

(56) References Cited

U.S. PATENT DOCUMENTS 7,535,070 B2 *  5/2009  Eshaghian-Wilner et al. ................. 257/421

OTHER PUBLICATIONS

Gayasen et al., "Exploring Technology Alternatives for Nano-Scale FPGA Interconnects," CAD 2005, Jun. 13-17, 2005, pp. 1-6.*
Tatas et al., "Architecture design of a coarse-grain reconfigurable multiply-accumulate unit for data-intensive applications," ScienceDirect, Feb. 11, 2006, pp. 74-93.*

* cited by examiner

*Primary Examiner* — Vuthe Siek

(57) ABSTRACT

The invention describes apparatuses for nano-scale integrated circuits applied to nanorobotics. Using EDA techniques, the system develops fully functional nano ICs, including ASICs and microprocessors. Three dimensional nano ICs are disclosed for increased efficiency in nanorobotic apparatuses. Nano-scale FPGAs are disclosed. The nano-scale semiconductors have applications to nano-scale and micro-scale robots.

8 Claims, 7 Drawing Sheets

SYSTEM, METHODS AND APPARATUSES FOR INTEGRATED CIRCUITS FOR NANOROBOTICS

CROSS-REFERENCES TO RELATED APPLICATIONS

The present application claims the benefit of priority under 35 U.S.C. §119 from U.S. Provisional Patent Application Ser. No. 60/865,605, filed on Nov. 13, 2006 and U.S. Provisional Patent Application Ser. No. 60/912,133, filed Apr. 16, 2007, the disclosures of which are hereby incorporated by reference in their entirety for all purposes.

FIELD OF THE INVENTION

The present invention pertains to the field of nanotechnology and nanorobotics. The system deals with epigenetic robotics applied to collectives of nanorobots. Specifically, the invention relates to nanoelectromechanical systems (NEMS), microelectromechanical systems (MEMS) and nanomechatronics. The invention also deals with the coordination of collectives of nanorobots and synthetic nanorobots, including synthetic assemblies of NEMS and synthetic nano-scale and micron-scale machine assembly processes. Applications of these systems and processes are made to nanoelectronics, bionanotechnology and nanomedicine.

BACKGROUND OF THE INVENTION

To date, four waves, or generations, of nanotechnology have evolved. The first generation was comprised mainly of developments involving chemical composition, such as new nanomaterials. The second generation developed simple tubes and filaments by positioning atoms from the ground up with novel machinery. The third generation developed nanodevices that perform specific functions, such as nanoparticles for the delivery of chemicals. Finally, the fourth wave has developed self-assembling nanoentities by chemical means.

The present invention represents a fifth generation of self-organizing collectives of intelligent nanorobotics. Self-organizing processes are possible at the nano- and micron-level because of the convergence of nanoelectronics developments and nanomechatronics developments.

While the first four generations of nanotechnology have been developed by theoretical scientists and inventors, the fifth generation of nanotechnology has been largely open until now. The present invention fills the gaps in the literature and in the prior art involving nanorobotics.

Early twentieth century theoretical physicists discovered that the simplest atoms were measurable at the nanometer scale of one billionth of a meter. In 1959, in his lecture "Race to the Bottom," the physicist Richard Feynman proposed a new science and technology to manipulate molecules at the nanoscale. In the 1970s Drexler's pioneering research into nanotechnology molecular-scale machinery provides a foundation for current research. In 1979, researchers at IBM developed scanning tunneling microscopy (STM) with which they manipulated atoms to spell the letters IBM. Also in the 1970s Ratner and his team at Northwestern developed the first nano-scale transistor-like device for nanoelectronics, which was developed into nanotransistors by researchers at the University of California at Berkeley in 1997. Researchers at Rice, Yale and Penn State were able to connect blocks of nanodevices and nanowires, while researchers at Hewlett Packard and UCLA were able to develop a computer memory system based on nano-assembly. Additionally, government researchers at NASA, NIST, DARPA and Naval Research have ongoing nanotechnology development projects, though these are mainly focused on nanoelectronics challenges. Finally, researchers at MIT, Cal Tech, USC, SUNY, Cornell, Maryland, Illinois and other universities in the U.S. have been joined by overseas researchers in developing novel nanotechnologies in order to meet Feynman's challenge.

Nanotech start-up ventures have sprung up to develop nanoscale crystals, to use as biological labels, for use in tagging proteins and nucleic acids (Quantum Dot) and to develop micro-scale arms and grippers by using MEMS to assemble manufacturing devices (Zyvex). Additionally, Nanosys, Nanometrics, Ultatech, Molecular Electronics, Applied Nanotech and Nanorex are ventures that have emerged to develop products in the nanotechnology market space. Until now, however, most of these businesses have focused son inorganic nanomaterials. Though a new generation of materials science has been aided by these earlier generations of nanotechnologies, the real breakthrough lies in identifying methods of developing intelligent systems at the nano-scale.

The two main models for building nanotechnology applications are the ground up method of building entities, on the one hand, and the bottom down method of shrinking photolithography techniques to the nanoscale. Both models present challenges for scientists.

In the case of the bottom up models, several specialized tools have been required. These include (a) atomic force microscopy (AFM), which uses electronics to measure the force exerted on a probe tip as it moves along a surface, (b) scanning tunneling microscopy (STM), which measures electrical current flowing between a scanning tip and a surface, (c) magnetic force microscopy (MFM), which uses a magnetic tip that scans a surface and (d) nanoscale synthesis (NSL), which constructs nanospheres.

In the case of the top down models, several methods and techniques have been developed, including (a) x-ray lithography, (b) ion beam lithography, (c) dip pen nanolithography (DPN), in which a "reservoir of 'ink' (atoms/molecules) is stored on top of the scanning probe tip, which is manipulated across the surface, leaving lines and patterns behind" (Ratner, 2003) and (d) micro-imprint lithography (MIL), which emulates a rubber stamp. Lithography techniques generally require the creation of a mask of a main model, which is then reproduced onto a substrate much like a semiconductor is manufactured. It is primarily through lithographic techniques that mass quantities of nanoentities can be created efficiently and cost-effectively.

The main patents obtained in the U.S. in the field of nanotechnology have focused on nanomaterials, MEMS, micro-pumps, micro-sensors, micro-voltaics, lithography, genetic microarray analysis and nano-drug delivery. Examples of these include a meso-microelectromechanical system package (U.S. Pat. No. 6,859,119), micro-opto-electro-mechanical systems (MOEMS) (U.S. Pat. No. 6,580,858), ion beam lithography system (U.S. Pat. No. 6,924,493), carbon nanotube sensors (U.S. Pat. No. 7,013,708) and microfabricated elastomeric valve and pump systems (U.S. Pat. No. 6,899,137 and U.S. Pat. No. 6,929,030). Finally, patents for a drug targeting system (U.S. Pat. No. 7,025,991) and for a design of artificial genes for use as controls in gene expression analytical system (U.S. Pat. No. 6,943,242), used for a DNA microarray, are applied to biotechnology. For the most part, these patents represent third and fourth generation nanotechnologies.

A new generation of nanotechnologies presents procedures for objects to interact with their environment and solve critical problems on the nano- and micron-scale. This generation of technology involves social intelligence and self-organization capabilities.

Biological analogies help to explain the performance of intelligent or self-organizing nanoentities. In the macro-scale environment, the behaviors of insects provides an important model for understanding how to develop models that emulate social intelligence in which chemical markers (pheromones) are used by individual entities to communicate a social goal. On the micro-scale, microbes and pathogens interoperate with the animal's immune system, in which battles either won or lost determine survival of the host. Other intracellular models show how proteins interact in order to perform a host of functions. At the level of DNA, RNA transcription processes are highly organized methods for developing cellular reproduction. These micromachinery processes and functions occur at the nanoscale and provide useful analogies for nanotechnologies.

In order to draw on these biological system analogies, complexity theory has been developed in recent years. Researchers associated with the Sante Fe Institute have developed a range of theoretical models to merge complexity theory and biologically-inspired processes, including genetic algorithms and collective behavior of economic agents.

Such a new nanotechnology requires distributed computation and communication techniques. It is, moreover, necessary for such a technology to adapt to feedback from its environment. The present invention presents a system in which these operations occur and specifies a range of important applications for electronics, medicine and numerous other areas. The main challenges to this advanced nanotechnology system lie in the discovery of solutions to the problems of limited information, computation, memory, communication, mobility and power.

Challenges

The development of a fifth generation of nanotechnologies faces several challenges. First, the manufacturing of nanoparts is difficult. Second, the assembly of nanoparts into functional devices is a major challenge. Third, the control and management of nanosystems is complex. Since physical properties operate differently at the nano-scale than at the macro-scale, we need to design systems that accommodate these unique physical forces.

The problems to identify include how to:
Build nanorobots
Connect nanodevices
Develop a nanorobotic power source
Develop nanorobotic computation
Develop specific nanorobotic functionality
Develop nanorobotic communication system(s)
Develop multi-functional nanorobotics
Activate nanorobotic functionality
Develop nanorobotic computer programming
Develop an external tracking procedure for a nanorobot
Develop an external activation of a nanorobot
Develop a hybrid control system for nanorobots
Use AI for nanorobots
Obtain environmental inputs via sensors

DEVELOPING SOLUTIONS TO THESE PROBLEMS

Most prior technological innovations for nano-scale problems have focused on the first generations of nanotechnology and on materials science. The next generation focuses on intelligent systems applied to the nano entities. This fifth generation of innovation combines the development of nanoscale entities with intelligence of complex systems.

Few researchers have devised solutions to these complex nano-scale problems. Cavalcanti has developed theoretical notions to develop a model of nanorobotics. However, these solutions are not practical and will not work in real situations. For example, there is not enough power of mobility in this model to overcome natural forces. Similarly, according to this theoretical approach, autonomous computation resources of nanorobots are insufficient to perform even the simplest functions, such as targeting. Without computation capacity, AI will not work at this level; without AI there is no possible way to perform real-time environmental reaction and interaction.

Cavalcanti's 2D and 3D simulations are dependent on only several variable assumptions and will not withstand the "chaos" of real environmental interactive processes. In addition, the structure of these nanorobots cannot be built efficiently from the bottom up and still retain critical functionality. Even if these many problems can be solved, individual nanorobots cannot be trusted to behave without error inside cells.

The emerging field of epigenetic robotics deals with the relations between a robot and its environment. This field suggests that it is useful to program a robot to learn autonomously by interacting with its environment. However, these models do not apply to groups of robots in which it is necessary to learn from and interact with many more variables in the robots' environment, including societies of other robots. In the case of groups of nanorobots with resource constraints, the present invention adds volumes to this promising field.

Solomon's research in developing hybrid control systems for robotic systems and in developing novel approaches for molecular modeling systems presents pathways to solving these complex problems. These novel research streams are used in the present invention.

Prior systems of robotics generally do not address the complexities of nanotechnology. The behavior-based robot system using subsumption methods developed by Brooks at MIT is useful for managing individual robot behavior with limited computation capacity. On the other end of the spectrum, central control robotic systems require substantial computation resources. Hybrid control robotic systems synthesize elements from these two main control processes. Even more advanced robotic control systems involve the integration of a multi-agent software system with a robotic system that is particularly useful in controlling groups of robots. This advanced robotic control system experiences both the benefits and detriments of the behavior-based model and the central control model.

The Nanorobotic Environment

The nano domain, which is a billionth of a meter, is measured in millionths of a meter. A single oxygen atom is roughly a single nanometer across. A micron is a millionth of a meter. The width of a human hair is about 60,000 nanometers.

The present invention focuses on the synthetic development of objects that are in a middle (meso-nano) sphere somewhat between the atomic size (micro-nano) of simple atoms and the mega-nano domain of micron-sized objects. While it is true that scientists have built, from the ground up, that is, atom by atom, objects such as elegant geodesic nanotubes made of carbon atoms, objects in this domain are too small and too expensive to construct to be useful for an active intelligent system. In order to be useful, a nanorobotic system requires numerous and economical robots dependent on mass production techniques that must generally be considered from the perspective of a top down strategy, that is, by utilization of largely lithographic procedures.

The nanorobotic entities described herein generally consist of objects with dimensions from 100 nm to 1000 nm (1 micron) cubed, but can be smaller than 100 nm or larger than ten microns. This size is relatively large by nanotechnology standards, but is crucial in order to maintain functionality. Keep in mind that a white blood cell is comprised of about 100,000 molecules and fits into this meso-nano domain. The micron-scale space of inter-object interaction may be comprehended by analogy to a warehouse in which nanoscale objects interact. In order to be useful, nanorobots require complex apparatus that includes computation, communications, sensors, actuators, power source and specific functionality, all of which apparatus requires spatial extension. Though this domain specification is larger than some of the atomic-scale research in nanotechnology, it is far smaller than most microelectronics.

While the larger meso-nano assemblies described herein possess a specific geometric dimensionality, the size dimensions of the domains in which they operate are also critical to consider. In these cases, each application has a different set of specifications. In the case of the human body, specific cells will have a dimensionality that is substantially larger than the complex molecular-size proteins that are constructed for interoperation within them.

Over time, however, it will be possible to make very small, useful micro-nano scale robots for use in intelligent systems. Thus, we may conceive of several generations of scale for these systems, the first being in the meso-nano domain.

SUMMARY OF THE INVENTION

The invention specifies nano-scale integrated circuits (ICs) with applications to nanorobotic electro-mechanical devices. The nano-ICs have microprocessor, ASIC or FPGA architectures. The IC architectures include computer memory, MAC components and interconnects that are designed with EDA software. The system also specifies nano-scale system on chip architectures.

The invention disclosed a class of nano-scale three dimensional ICs. By stacking layers of ICs onto 3D chips using through silicon vias (TSVs) and multilayer CMOS fabrication techniques, the nano-MPs, nano-ASICs and nano-FPGAs of the present invention maximize performance and efficiency.

The chips are applied to nanorobotics. By integrating nano-scale ICs into nanorobots, the nanorobot devices obtain intelligence functionality that includes data analysis, memory access, sensor access, communications control and mobile control.

The ICs process program code by employing software agents and by interacting with external computation. Specifically, the system uses genetic algorithms and reduced instruction AI techniques to overcome computing resource constraints.

The present system is also applied to microrobots and to devices that integrate MEMS.

ADVANTAGES OF THE INVENTION

Use of nano-scale ICs provide intelligence functionality to nanorobots and microrobots.

By combining multiple nanorobots into collectives, the use of nano-scale ICs allow grid computing capabilities that allow social intelligence capabilities with numerous applications to electronics and biology.

DESCRIPTION OF THE INVENTION (I) Integrated Circuits in Nano-Robots

In order to achieve intelligence, it is necessary for nano-scale and micron-scale robotic entities to embody integrated circuits. While trends in ICs have focused on generating the fastest chips with billions of transistors, the current system seeks to develop extremely small, yet highly functional, circuits for use in nanorobots. By interoperating with multiple nanorobots, the intelligent robots are organized into collectives similar to the grid computing paradigm.

One main model for nanorobotic ICs is the traditional two dimensional chip approach which employs microprocessor architectures, such as RISC, ASIC and complex programmable logic device (CPLD), such as FPGA architectures. This model integrates logic and memory components using traditional interconnects onto devices in different chip configurations according to each application preference.

Another model employs a new generation of efficient three dimensional IC architectures. This approach stacks layers of ICs by using through silicon vias (TSVs) to connect the layers. This model is useful to create micron-scale and nano-scale 3D system on chip (SoC) technologies that are applicable to nanorobotics. This approach leads to the system on a nano chip (SoNC) model disclosed herein.

Because the model employs multiple nanorobots in collectives in order to be functionally useful, the present invention uses heterogeneous computing options to maximize functionality. For example, collectives of nanorobots are comprised of nanorobots that include multiple types of ICs, including ASICs, MPs, FPGAs and active storage devices that integrate logic and memory in different ways in order to optimize specific tasks. By working together in collectives using a division of labor enabled by multiple computing types, the present system maximizes computability at the ultra small scale.

Micron-scale computing exists. Hitachi has produced a family of micron-scale chips that measure 0.4 mm squared. The "super-micro" chips are used for radio frequency identification (RFID) applications. Since they contain read only memory exclusively, their functionality is highly restricted.

However, with the advent of smaller transistors made possible by novel lithographic techniques, next generation ICs will be capable of very small size. In a sense, rather than seeking ever faster computing capability with more and more transistors in order to maintain Moore's law, the present system seeks to go back to the origins of the integrated circuit.

The first microprocessors, such as the Intel 8080, used only 4500 transistors and were capable of 200K operations per second. The Motorola MC6800 used 200K transistors and achieved substantial functionality.

The present system is able to achieve capabilities between 4,000 and 1,000,000 transistors within nano-scale and micron-scale integrated circuits, respectively, in both 2D and 3D embodiments, in order to be useful within nanorobots and micron-scale robots.

While 45 nm transistors are used in ICs, 32 nm, 26 nm, 22 nm, 16 nm and 10 nm scale transistors have been constructed using novel lithographic techniques. For 22 nm transistors high index immersion lithography is used and for 16 nm transistors high index immersion lithography is combined with double patterning techniques. 10 nm and 16 nm transistors are comprised of 3D fin field effect transistors (FETS). These classes of ICs are designed using CMOS fabrication techniques.

(1) Nano-Scale Integrated Circuit for Nanorobots Using EDA Processes

Electronic design automation (EDA) techniques are used in the chip architectural process. Transistors are organized in logic and memory components of integrated circuits by using layout and routing of interconnects with EDA.

Nano-scale ICs are designed as simple modular combinations of logic and memory components. By organizing a family of N-ICs, EDA techniques develop optimal options with 4,000 to 10,000 transistors. These small chip options, whether ASIC, FPGA microprocessor or hybrid, deliver multiple functionality for nanorobots. Very simple MP functionality is supplemented by combining multiple nanorobots into collectives that share computation, communications and software.

Chips at the submicron scale are designed in CMOS by using lithographic fabrication techniques. The 2D model N-IC results in "flat" chips that are useful in some nanorobotic applications, particularly for the simplest computational functions.

These chips contain 16-bit or 32-bit RAM and 256-byte or 512-byte ROM memory components and are capable of 8-bit, 16-bit or 32-bit computation functionality.

Because they are SoNCs, they also contain analog functionality (ADC and DAC), sensors and communications functionality on the chip as well as logic and memory capability.

(2) Three Dimensional Nano-IC for Nanorobots

Three dimensional ICs possess increased functionality in an efficient space than traditional 2D ICs. 3D chips stack 2D layers of ICs and are constructed using CMOS layering techniques in fabrication. The 3D chip architecture allows organization of memory and logic on tiles of each layer and thereby increases the options for chip design in order to optimize chips for multiple applications. These hybrid N-ICs provide an ideal application to nanorobotics.

By constructing a layer of a 3D N-IC with 26 transistors by 26 transistors, or 676 transistors on a single layer, and by stacking eight layers using CMOS technology, the 3D N-IC are comprised of a total of 5408 transistors, yet are contained in a compact space with an 4:1 aspect ratio. Only a small deviation of one less transistor per row yields a 25 by 25 transistor layer (525 transistors on a single layer) and 4200 transistors on an 8 layer N-IC.

In substantially larger 3D N-IC chips, 200 transistors by 200 transistors comprise a single layer of 40K transistors, with a total of 200K transistors in a 5 layer N-IC. With an average transistor size of 22 nm (averaging 16 nm and 26 nm), the total space used is approximately 4400 nm squared (19, 360,000 nm square). This chip is capable of 6 MIPS. Similarly, using 100 by 100 transistors yields a 10,000 transistor layer. Nine layers of this chip produces a 90K transistor 3D N-IC capable of 3.6 MIPS. This chip is approximately 2200 nm squared (4,840,000 nm square). Finally, 258 by 258 transistors produces 66,666 transistors per layer. Stacking 12 layers produces an 800K transistor meso N-IC device capable of 24 MIPS.

3D N-ICs may be MPs, ASICs, FPGAs, active storage devices or hybrids.

(II) Nano-Scale FPGAs

Field programmable gate arrays (FPGAs) are either deterministic or indeterministic. Deterministic FPGAs are used to oscillate between various application specific integrated circuit positions in order to adapt to a changing environment. Indeterministic FPGAs will operate continuously until they solve a particular problem. These continuously programmable FPGAs (CP-FPGAs) are used for rapid prototyping in the field thereby enabling them to interact with an evolving environment.

(1) Nano-FPGAs (N-FPGAs)

Given the steady increase in semiconductor speed and steady decrease in size, the design of nano-scale FPGAs is achievable.

The present invention specifies an FPGA in which there is continuous transformation of the configuration of the gate arrays in order to solve problems at the nano-scale. Among other applications, N-FPGAs will be used within nano-robots in order to more rapidly interact with an evolving environment. While N-FPGAs are used within the nanorobots to provide computational functionality, the gates of the N-FPGAs are comprised of nano-scale objects and interconnects.

Since the N-FPGA is indeterministic in order to maintain maximum functionality in evolutionary environments, it is necessary to have a way to track the record of its evolution. The present system therefore has a mechanism to track the evolvability pattern of the N-FPGA in order to record its transformational pathways by exporting its sequential evolution of structural transformation to an external computer for analysis. This method of tracking the indeterministic N-FPGA, by using communications links and modeling processes, eliminates the need to reverse-engineer the specific pattern of the evolution of the gate structures over time. By creating a communications interface that tracks the gate structure evolution process using an external computer, the system provides additional environmental data and activates the N-FPGA by employing external macro-computation as well.

(2) Evolutionary N-FPGAs

Because they are comprised of nano-scale parts, N-FPGAs "evolve" on-demand by combining autonomous programmable modular components and logic arrays in order to expand functionality. For example, this autonomous modularity of components facilitates whole memory sections of a chip while the chip is operational. This allows a new dimension of nano-scale evolvable hardware (N-EHW) in which whole new sections of the chip autonomously evolve. This embodiment of the present invention is critical in order to establish self-repairing hardware on the nano- and micron-scale. With this process it is possible to engage in the limited replication of a semiconductor in the field, for the purpose of repairing hardware. This view presents an embryonic model of electronics N-EHW. The development of a micro-scale artificial brain is a consequence of this view of evolutionary semiconductors.

By using the N-EHW CNR features of self-assembly and reaggregation, the present invention provides methods for FPGAs' to add sections and functional capacity akin to an evolving artificial brain. This would be similar to the development of a brain from a child to that of an adult in which the modular aggregated N-FPGA network co-adapts to its evolving environment and constantly learns as it grows in order to continually optimize its performance.

(3) Networks of N-FPGAs

Networks of N-FPGAs operate within a CNR system. The N-FPGAs have external linkages between nanorobot nodes. The N-FPGAs are the artificial brains of the nanorobots and are linked together into a network by a communications system that uses software agents in a multi-agent system. In networks of N-FPGAs in CNRs, the nanorobots that are not functional represent bottlenecks around which the network reroutes communications. The N-FPGA and CNR network achieves a level of operational plasticity by constantly rerouting its arrangement in order to optimize solutions.

By linking together the N-FPGAs into a computer network, the computational capacity of the CNR system substantially increased.

In another embodiment of the present system, N-FPGAs are not contained within the nanorobots, but rather function as central modules CNRs may access. These micro-FPGAs are centralized for use by a single CNR team or a combination of teams. These FPGAs behave as the main computer server for the multitude of nanorobots in the collective. The FPGAs appear as centralized modules that are physically adjacent to the CNR teams.

In yet another embodiment of the system, micro- or nano-FPGAs are replaced by micron- or nano-scale microprocessors.

In still another embodiment of the invention, the system uses external computing resources that are accessed through the communication system by the use of software agents.

(4) Interaction of N-EHW CNRs and N-FPGAs

One of the main advantages of utilizing FPGAs is to adapt the hardware to an environment based on feedback from the environment as it changes. Similarly, the advantage of the N-EHW is to adapt to feedback from an evolving environment.

The feedback from, and adaptation to, the environmental changes activate the transformational processes of both the N-FPGAs and the N-EHWs. The new position of the N-EHW apparatus then transforms its configuration and accepts new information from the environment and continues to transform in new ways to adapt to the changing environment and so on. The next stage input of the environment will then stimulate the N-FPGA transformation, which will then respond to the environmental change, which, in turn, will stimulate a transformation in the structural configuration of the N-EHW apparatus. This process of co-evolutionary transformation will continue to oscillate for numerous phases.

These co-evolutionary and adaptive processes will continue until optimal solutions are achieved. These complex dynamics of the N-EHW and N-FPGA systems will solve key molecular biology problems.

As the functional utility of the N-EHW operates in the environment, the structural apparatus of the N-EHW system will act upon and change the environment. The rate of change in the environment will therefore be reduced as the N-EHW performs its function, and thus the N-EHW and the N-FPGA interactions will achieve a relative position of equilibrium in the self-organizing and self-assembling systems.

Reference to the remaining portions of the specification, including the drawings and claims, will realize other features and advantages of the present invention. Further features and advantages of the present invention, as well as the structure and operation of various embodiments of the present invention, are described in detail below with respect to accompanying drawings.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes in their entirety.

DETAILED DESCRIPTION OF THE DRAWINGS

In order for nanorobots to have functionality, they require intelligence made possible by integrated circuitry. The three main models for semiconductors are application specific integrated circuits (ASICs), microprocessors (MPs) and complex programmable logic devices (CPLDs), the most prominent of which are field programmable gate arrays (FPGAs).

While most electronics IC components have grown to include billions of transistors, made possible by lithographic fabrication techniques to shrink the size of transistors, the present invention uses the development of nano-scale transistors to produce small nano-scale ICs. These minimalist ICs perform specific functionality associated with the first generation of useful MPs and ASICs, yet are in a tiny package that is integrated into nanorobotic apparatuses.

In addition to traditional two dimensional IC development, the present system also integrates the development of three dimensional ICs, which are more efficient and space saving than 2D components.

Figure 1:
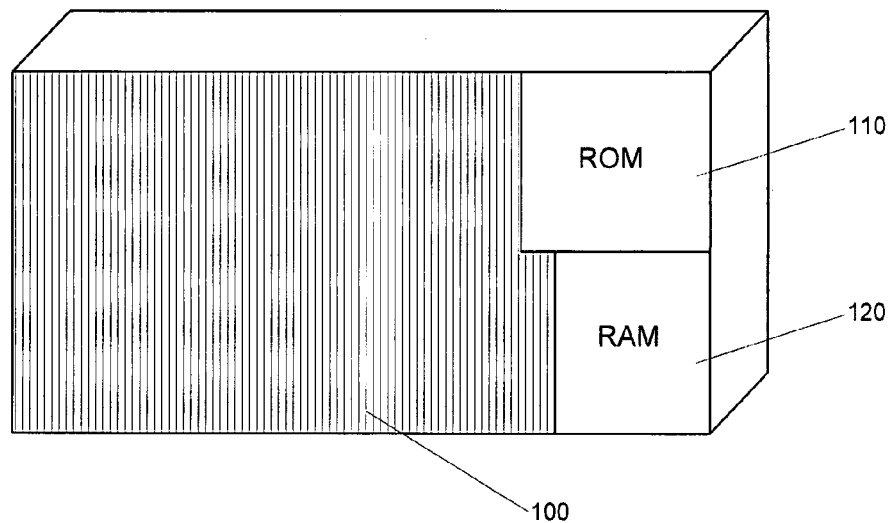
FIG. 1 is a schematic diagram of a nano-scale integrated circuit.

FIG. 1 illustrates the top view of a three dimensional nano-scale IC (100) which has a section for ROM (110) and RAM (120). The lines illustrate rows of transistors.

Figure 2:
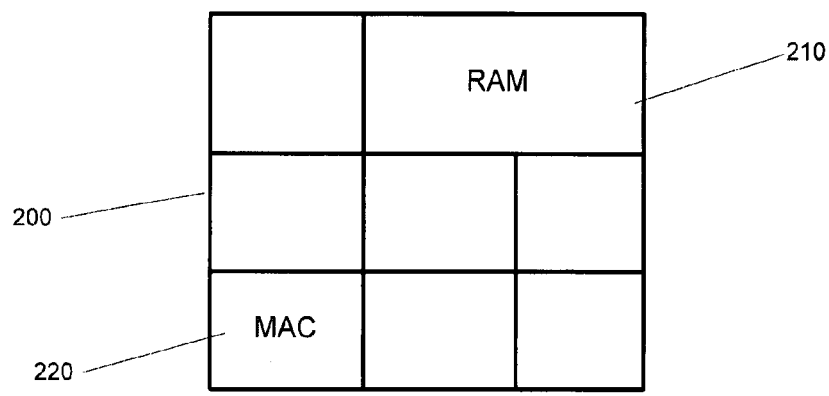
FIG. 2 is a schematic diagram of an integrated circuit illustrating main sections.

In FIG. 2, a top view of an IC (200) is illustrated with an emphasis on showing the sections of the layer of the IC. The RAM component (210) is shown and the multiply accumulate convert (MAC) component (220) is shown in differentiated sections.

Figure 3:
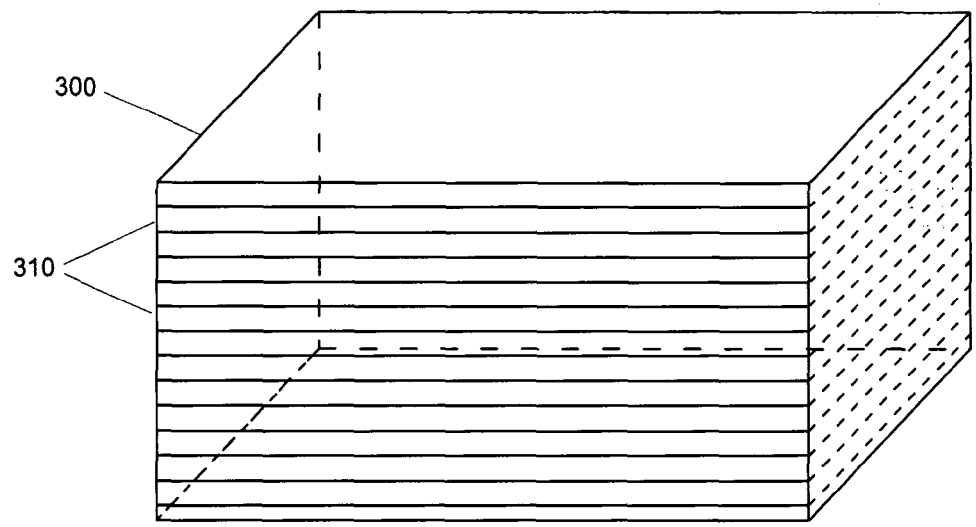
FIG. 3 is a schematic diagram of a three dimensional nano-scale integrated circuit.

FIG. 3 shows a three dimensional IC (300) with fourteen layers (310). 3D ICs provide a way to combine multiple layers for increased functional efficiency.

Figure 4:
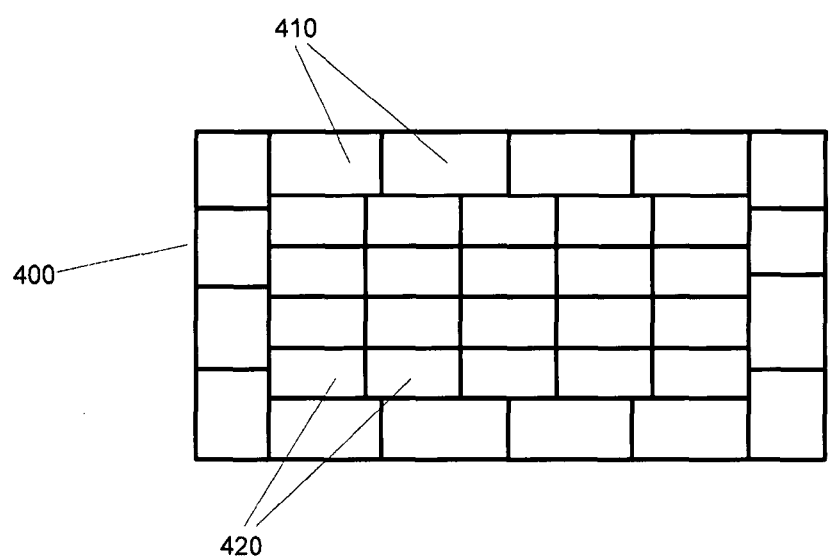
FIG. 4 is a diagram of a top view of the tiles of a nano-scale FPGA.

FIG. 4 shows a top view of the tiles on an FPGA layer (400). The outer layer shows 16 tiles (410) on which look up tables (LUTs) and ROM components are situated. The inner layer has 20 tiles (420) on which logic arrays are situated. The logic arrays have gates that change position to transform from one ASIC position to another in order to solve computational problems.

Figure 5:
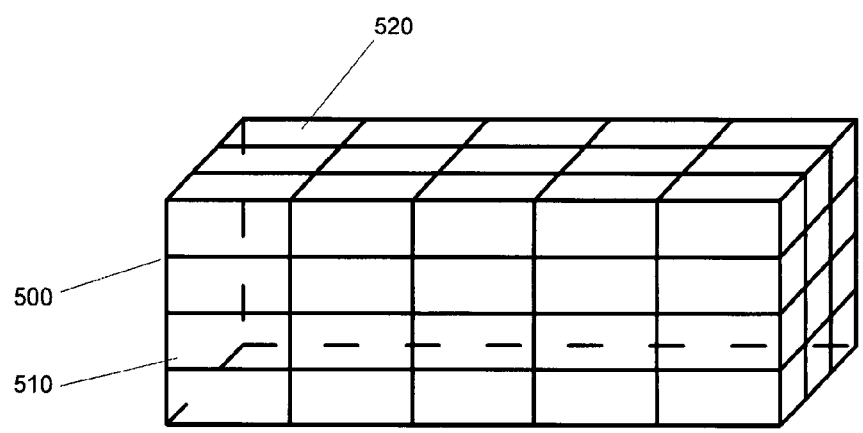
FIG. 5 is a schematic diagram of a four layer three dimensional nano-scale IC with fifteen sections on each layer.

FIG. 5 shows an IC (500) comprised of a stack of four layers (510), with fifteen tiles on each layer (520).

Figure 6:
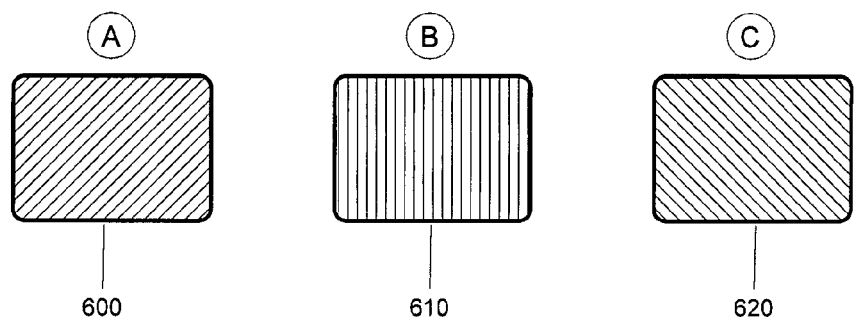
FIG. 6 is a set of diagrams illustrating the sequence of an evolvable logic array.
Figure 7:
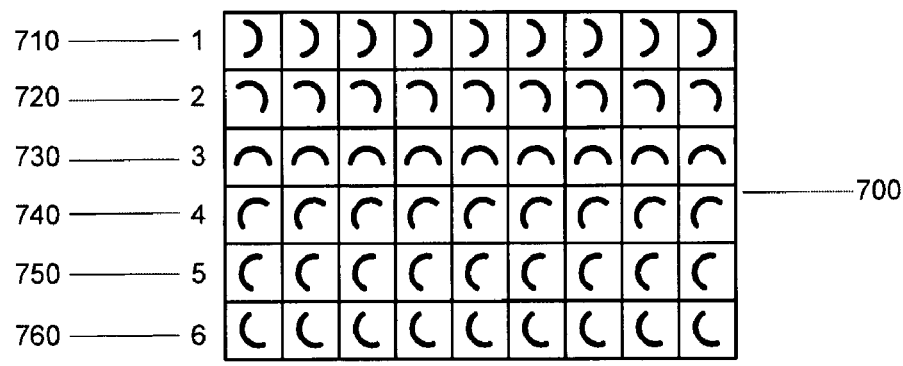
FIG. 7 is a schematic diagram of a top view of a grid of evolvable logic gates shifting positions in a process of evolution.
Figure 8:
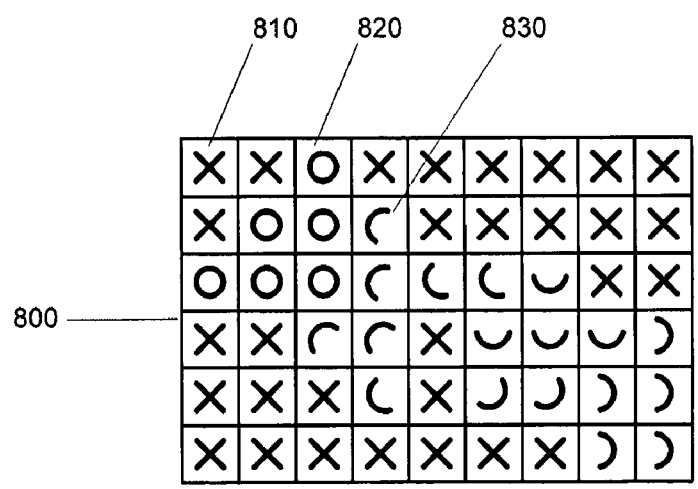
FIG. 8 is a schematic diagram of a top view of an evolvable logic array illustrating the transformed position of the specific logic gates.

FIGS. 6, 7 and 8 show the changed positions of the FPGA. FIG. 6 shows three main positions (A, B and C) illustrating the alternating positions of an evolvable logic array from position at 600 to position 610 to position 620. FIG. 7 shows the different positions of each layer (1 through 6 at 710 through 760) of a six layer FPGA (700). FIG. 8 shows a top view of a conversion process of a layer of an FPGA (800) as its logic array gates change from one position to another. In this dynamic sequence, the logic array gates continue to change their positions until they achieve the ASIC position. In some embodiments, this process of changing the position of gate arrays to various ASIC positions will continue until a computational problem is solved. In one view, this representation shows the cross section of the changing of a cellular automata process with each symbol referring to a temporary state feature (810, 820 and 830).

Figure 9:
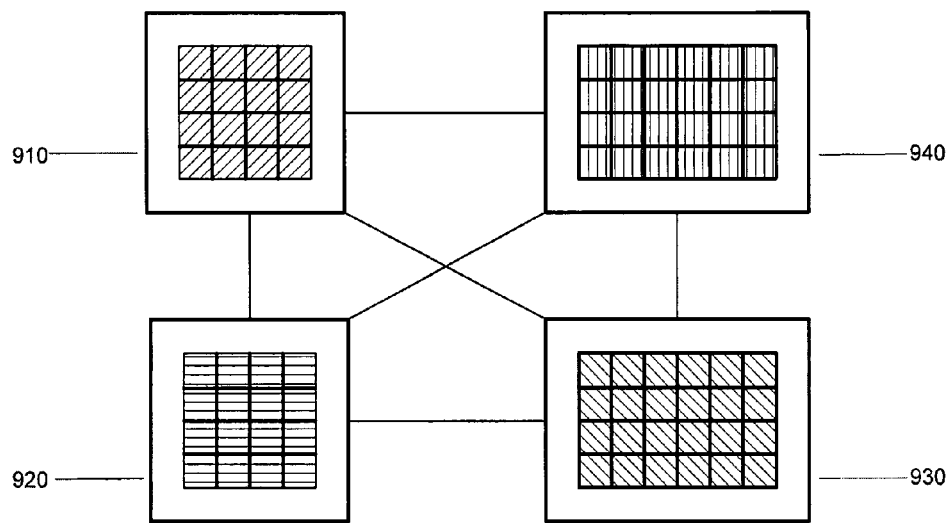
FIG. 9 is a schematic drawing of the top view of four layers of evolvable logic arrays in different positions.

FIG. 9 illustrates the connection between four FPGAs (910, 920, 930 and 940) which are shown in different simultaneous positions.

Figure 10:
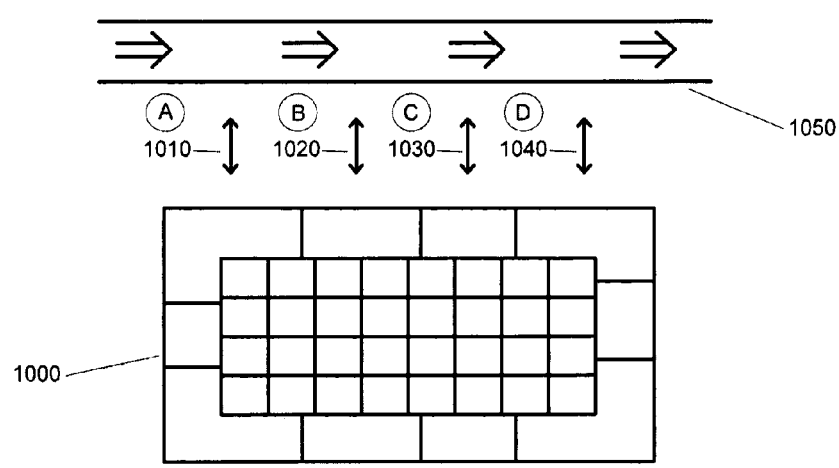
FIG. 10 is a schematic drawing of the top view of an FPGA layer of an IC in the context of interaction with environmental change.

FIG. 10 shows a top view of an FPGA layer (1000) with a reference to the changing environment. The FPGA will change positions in reaction to the changed inputs from the changing environment. At A (1010), an initial position will begin the process of changing the position state of the FPGA. As the environment changes (1050), the position B (1020) will alter the position of the gate array in the FPGA. This process continues as the environment continues to change at C (1030) and D (1040). The changing of the positions of the FPGA gate arrays effectively reprograms the IC. As the chip is reprogrammed, it performs a new set of functions that interact with the environment. This interaction process provides a feedback loop.

Figure 11:
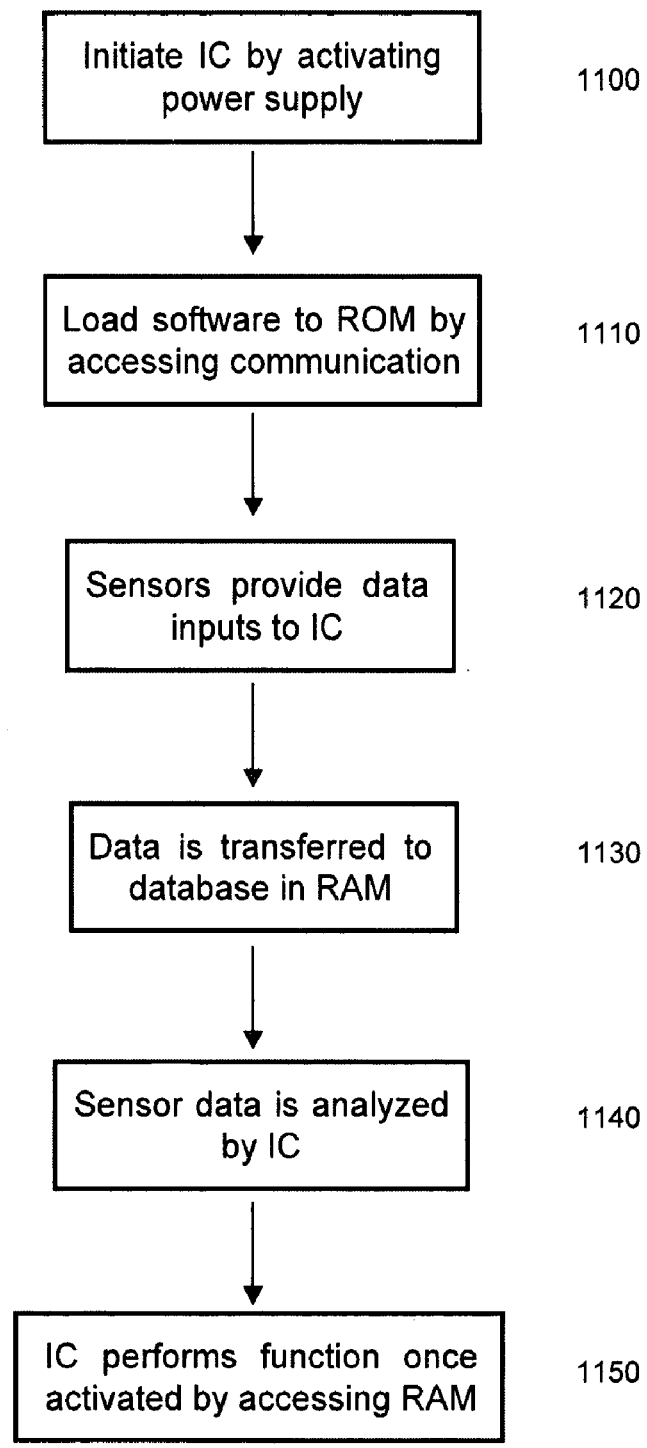
FIG. 11 is a flow chart showing the process of analyzing sensor data by an FPGA.

FIG. 11 shows a flow chart which describes the initial process of repositioning the FPGA. After the power supply activates the IC (1100), software is loaded to ROM (1110) and sensors provide data inputs to the IC (1120). Data is transferred to the database in RAM (1130) and sensor data is analyzed by the IC (1140). Finally, the IC performs a function once activated by accessing the RAM (1150).

Figure 12:
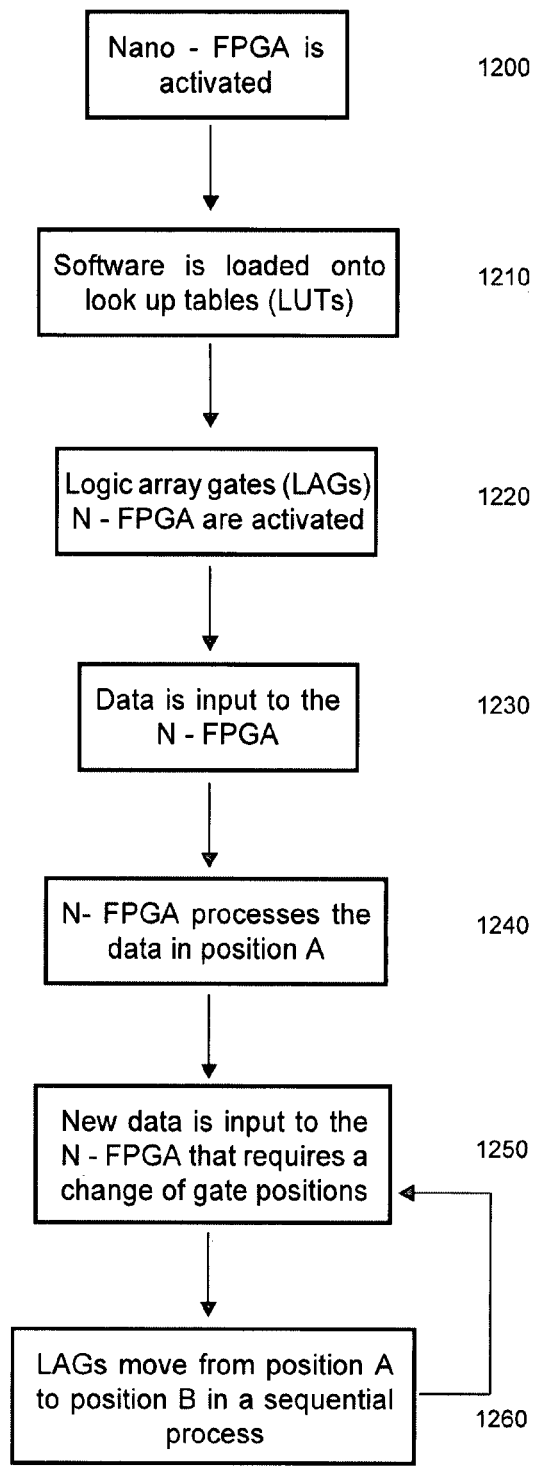
FIG. 12 is a flow chart showing the processing of an FPGA.

In FIG. 12, the process of FPGA operation is shown. Once the FPGA is activated (1200), software is loaded onto the look up tables (1210) and the logic array gates are activated (1220). Data is input to the FPGA (1230) and the FPGA processes the data in an initial position (1240). New data is input into the FPGA that requires a change of gate positions (1250) and the logic array gates move from position A to position B in a sequential process (1260). The process then repeats as new information is made available, which stimulates a transformation of the logic array gate positions. This process repeats until a specific problem is solved.

I claim:

1. A system for a nano-scale FPGA, comprising:
   a series of rows of nano-scale gates that are arrayed on a silicon substrate and that are configured into logic array grids;
   look up tables (LUTs) in memory components on the periphery of a nano-scale device:
   nano-scale connectors between gates;
   wherein a routing of logic arrays is done by using nano-scale connectors between the gates;
   wherein the gates are structured into grids of evolvable logic arrays;
   wherein the logic array grids access LUTs;
   wherein the logic array grids access memory on the periphery of the device;
   wherein the gates reconfigure to a different position when initiated;
   wherein the device contains between 1,000 and 10,000 gates;
   wherein the device reconfigures its gates in response to feedback from its environment;
   wherein the environment is electronic, biological or chemical; and
   wherein the environment provides feedback to the device.

2. A system of claim 1:
   wherein the nano-scale FPGAs are organized to send and receive messages;
   wherein two or more nano-scale FPGAs communicate with each other by linkage in a network;
   wherein the network of nano-scale FPGAs coordinate their behaviors;
   wherein the network of nano-scale FPGAs receive inputs from an indeterministic environment;
   wherein the network of nano-scale FPGAs analyze the inputs from the indeterministic environment;
   wherein the nano-scale FPGAs in the network restructure their configurations to optimally respond to the environment; and
   wherein the nano-scale FPGAs in the network continue to update their restructuring to the most recent environmental changes.

3. The system of claim 2:
   wherein when the network of nano-scale FPGAs interacts with the environment and receives external inputs, the nano-scale FPGAs restructure their gate configurations;
   wherein the nano-scale FPGAs perform computational functions in response to the external inputs; and
   wherein the nano-scale FPGAs adapt to environmental changes.

4. The system of claim 2:
   wherein the network of nano-scale FPGAs use software agents in a multi-agent system to pass messages.

5. The system of claim 2:
   wherein the network of nano-scale FPGAs are integrated in a network of nanorobots.

6. The system of claim 5:
   wherein the network of nanorobots contain sensors to sense inputs;
   wherein the network of nanorobots interact with an indeterminate environment by using computation from nano-scale FPGAs; and
   wherein the network of nanorobots transform their aggregate network configuration to adapt to environmental changes.

7. The system of claim 1;
   wherein the nano-scale FPGA is organized to analyze data and receive data inputs; and
   wherein when the environmental conditions change the device tracks the changes.

8. The system of claim 1:
   wherein the nano-scale FPGA in installed in a nanorobotic device that contains an actuator to perform at least one function; and
   wherein the nano-scale FPGA is organized to activate the actuator in the nanorobot to perform a function.

* * * * *